United States Patent [19]

Seto et al.

[11] Patent Number: 5,629,207
[45] Date of Patent: May 13, 1997

[54] METHOD OF CONTROLLING TEST FILMS IN BIOCHEMICAL ANALYSIS APPARATUS

[75] Inventors: Yoshihiro Seto; Toshimi Furuya, both of Kanagawa-ken, Japan

[73] Assignee: Fuji Photo Film Co., Ltd., Kanagawa, Japan

[21] Appl. No.: 364,271

[22] Filed: Dec. 27, 1994

[30] Foreign Application Priority Data

Dec. 27, 1993 [JP] Japan ................. 5-331123

[51] Int. Cl.$^6$ ........................ G01N 35/10
[52] U.S. Cl. ............... 436/50; 436/43; 436/44; 436/46; 436/55; 422/63; 422/64; 422/66; 422/67; 422/105; 422/119; 414/416; 294/64.1
[58] Field of Search ................. 436/43, 44, 46, 436/50, 55; 422/63, 55, 64, 65, 66, 67, 99, 105, 108, 119; 414/416; 294/64.1

[56] References Cited

U.S. PATENT DOCUMENTS

| | | | |
|---|---|---|---|
| 3,848,962 | 11/1974 | Nelson | 350/86 |
| 3,999,795 | 12/1976 | Barker | 294/64 R |
| 4,683,654 | 8/1987 | Scholten et al. | 29/832 |
| 4,750,768 | 6/1988 | Kumar | 294/64.1 |
| 4,807,984 | 2/1989 | Kurimura et al. | 350/529 |
| 5,284,334 | 2/1994 | Yamamoto | 271/107 |
| 5,308,132 | 5/1994 | Kirby et al. | 294/64.1 |
| 5,324,087 | 6/1994 | Shimose et al. | 294/64.1 |

FOREIGN PATENT DOCUMENTS

| | | |
|---|---|---|
| 0064691 | 11/1982 | European Pat. Off. . |
| 0555654 | 8/1993 | European Pat. Off. . |
| 05177056 | 2/1995 | Japan . |

*Primary Examiner*—Long V. Le
*Attorney, Agent, or Firm*—Sughrue, Mion, Zinn, Macpeak & Seas

[57] ABSTRACT

In a biochemical analysis apparatus a frameless dry chemical analysis film having a reagent layer formed on a support sheet is taken out from a cartridge storing therein a plurality of the frameless chemical analysis films, applied with a sample liquid, inserted into an incubator and taken out from the incubator and at least a part of these steps and film transferring steps between these steps is effected with the film held by a suction pad. A change of pressure in the suction pad when it attracts the film under a suction force is measured and the attracting state of the suction pad is judged on the basis of the result of the measurement. The part of the steps which is effected with the film held by the suction pad is controlled on the basis of the judgment.

8 Claims, 6 Drawing Sheets

F I G. 7
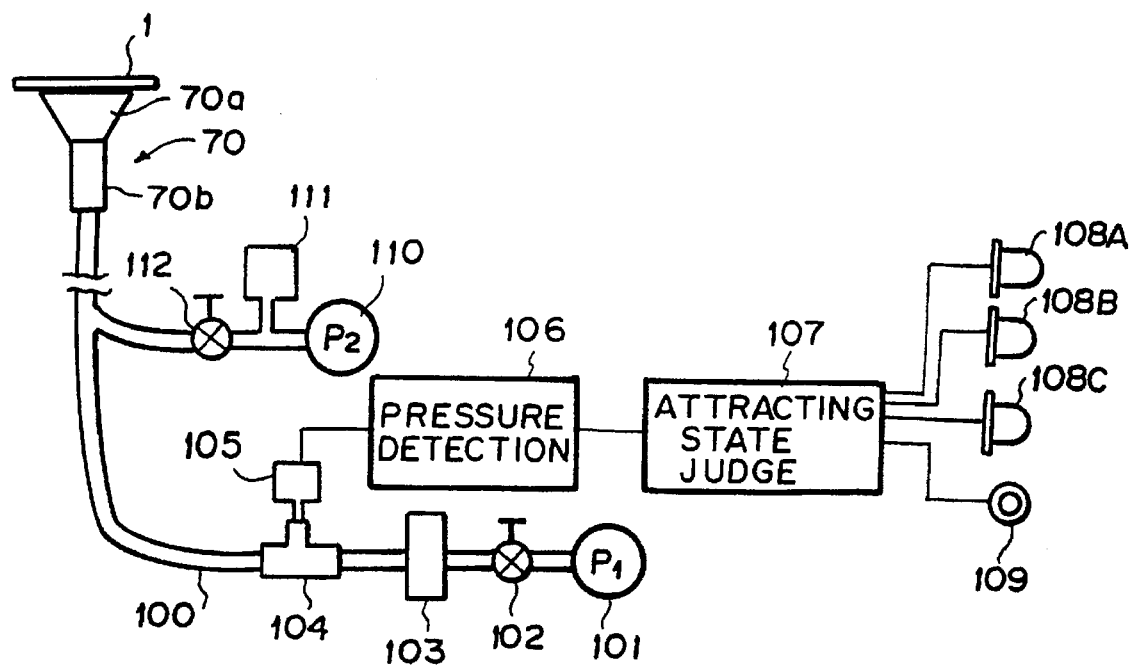

F I G. 8A
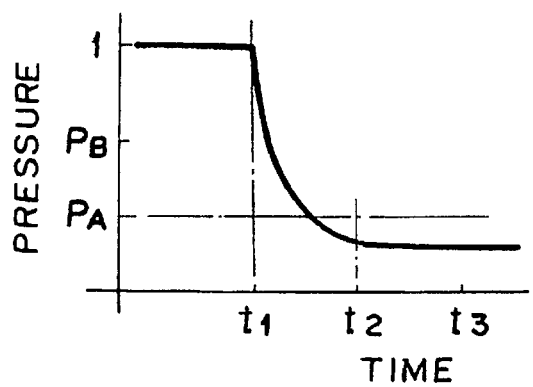
F I G. 8B
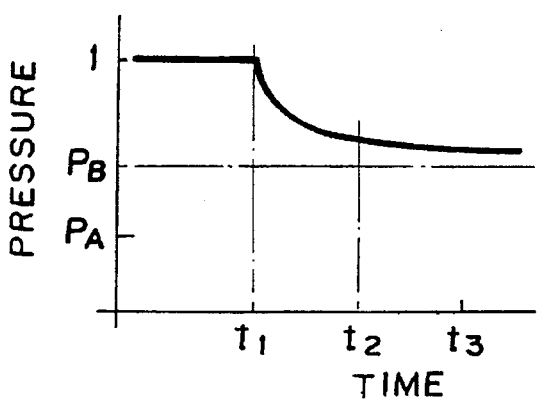
F I G. 8C
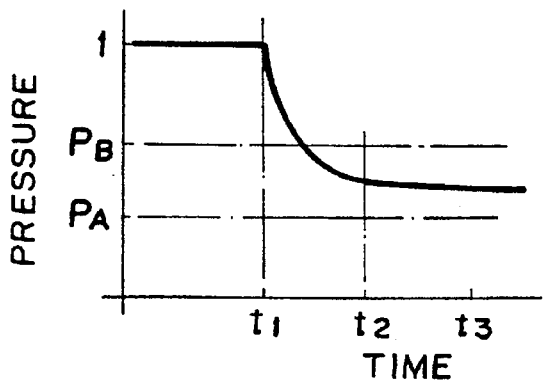
F I G. 8D
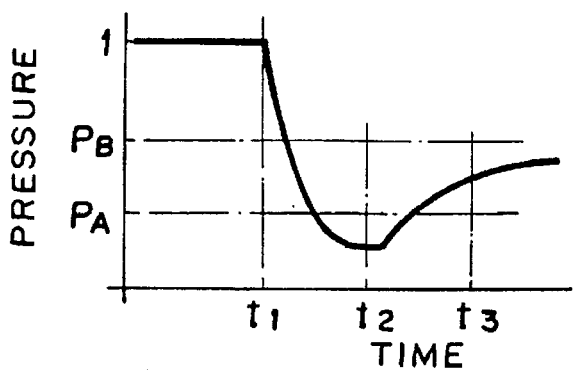

METHOD OF CONTROLLING TEST FILMS IN BIOCHEMICAL ANALYSIS APPARATUS

BACKGROUND OF THE INVENTION

1. Field of the Invention

This invention relates to a biochemical analysis apparatus and a method of controlling same, and more particularly to controlling a biochemical analysis apparatus in which a frameless dry chemical analysis film having a reagent layer containing a reagent whose optical density changes through a chemical reaction, a biochemical reaction, an immunoreaction or the like with a specific biochemical component contained in a sample liquid such as blood or urine is taken out from a cartridge, transferred to a sample liquid spotting position, applied with a sample liquid by spotting in the sample liquid spotting position, transferred to an incubator, inserted into the incubator and taken out from the incubator and at least one of these steps is effected with the film held by a suction means.

2. Description of the Prior Art

There has been put into practice a "dry-to-the-touch" chemical analysis film with which the content of a specific chemical component contained in a sample liquid, the activity thereof or the content of a solid component can be quantitatively analyzed by only spotting a droplet of the sample liquid on the film. One example of a dry chemical analysis film, there has been known an integrated multi-layered chemical analysis film (sometimes referred to as "multi-layered chemical analysis element") comprising a support sheet of organic polymer and at least one reagent layer which contains a reagent and is formed on the support sheet. A spreading layer is sometimes provided over the reagent layer. Further, a dry chemical analysis element which is formed of filter paper and has one or more layers has been proposed and partly put into practice.

When quantitatively analyzing the chemical components or the like contained in a sample liquid using such a dry chemical analysis film, a droplet of the sample liquid is typically spotted on the film (on the spreading layer when the film is provided with a spreading layer and on the reagent layer when the film is not provided with a spreading layer) and is held at a constant temperature for a predetermined time (incubation) in an incubator so that a coloring reaction occurs. The optical density of the color formed by the coloring reaction is then optically measured. That is, a wavelength is pre-selected according to the combination of the component to be analyzed and the reagent contained in the reagent layer of the film. Measuring light containing this wavelength is then projected onto the film and the optical density of the film is measured. Then the concentration or the activity of the component to be analyzed is determined on the basis of the optical density using a calibration curve which represents the relation between the concentration of the biochemical component and the optical density.

The integrated multi-layered chemical analysis film is generally in the form of a film chip of a predetermined shape, e.g., as square or rectangle. The film chip is sometimes provided with a frame of organic polymer and used in the form of a chemical analysis slide. The frame helps to flatten the film chip which is apt to curl or warp in a dry state, thereby facilitating automated handling of the chemical analysis film. However use of the chemical analysis slide is disadvantageous in that the chemical analysis slide is larger than the chemical analysis film chip by the size of the frame and accordingly parts of the biochemical analysis apparatus must be larger, which obstructs reduction in size of the biochemical analysis apparatus and at the same time results in reduction of the overall throughput capacity of the biochemical analysis apparatus. Thus, the use of the chemical analysis slides adds to the cost of measurement.

In a biochemical analysis apparatus we have proposed previously, the film chip is used without a frame (hereinafter referred to as "frameless chemical analysis film"). A plurality of the frameless chemical analysis films are loaded in a cartridge and the cartridge is loaded in a chemical analysis film supplier for a biochemical analysis apparatus. The frameless chemical analysis films are taken out from the cartridge in the supplier one by one by use of a suction pad as disclosed, for instance, in our patent applications such as Japanese Patent Application No. 5(1993)-177056 and U.S. Patent Application No. 08/273,131, now U.S. Pat. No. 5,534,224.

Since the frameless chemical analysis film is curled or warped into a roof tile-shape in the dry state, taking out the film by attracting it under a suction force by the suction pad as described above should be the best way of taking out the film from the cartridge without damaging the surface of the film.

In the biochemical analysis apparatus, the frameless chemical analysis film taken out from the cartridge is transferred to the spotting position and a sample liquid is spotted on the film. Thereafter the film is transferred to the incubator and inserted into a cell in the incubator. After a predetermined incubation, the optical density of the biochemical substance is measured, and the film is taken out from the cell and discarded in a predetermined discarding box. In many of these steps, a plurality of suction means, e.g., suction pads and horseshoe-like suction means, are used to hold the frameless chemical analysis film. The suction pads and the horseshoe-like suction means are disclosed in detail in the Japanese patent applications identified above and the like.

Since the suction means must surely hold the frameless chemical analysis film which is light in weight and small in thickness, it is necessary to constantly keep the suction force at an optimal level. However, the suction force can be easily changed by various causes, such as a clog in the suction pipe from dust, defects in the vacuum pump, valves, filters or the like, and/or cracking in the suction means etc.

Further, since many suction means are used in the biochemical analysis apparatus, it is difficult for the operator to constantly check the suction force of each suction means.

SUMMARY OF THE INVENTION

In view of the foregoing observations and description, the primary object of the present invention is to provide a method of controlling a biochemical analysis apparatus which can constantly watch the attracting state of the suction means.

Another object of the present invention is to provide a method of controlling a biochemical analysis apparatus which can inform the operator when the attracting state of the suction means is abnormal.

Still another object of the present invention is to provide a method of controlling a biochemical analysis apparatus which can quickly remove dust or the like when the attracting state of the suction means is abnormal due to dust, etc. clogging the suction means.

In accordance with the present invention, there is provided a method of controlling a biochemical analysis apparatus in which a frameless dry chemical analysis film having a reagent layer formed on a support sheet is taken out from a cartridge, applied with a sample liquid, inserted into an incubator and taken out from the incubator, and at least a part of these steps and film transferring steps between these steps is effected with the film held by a suction means, is Furthermore a change of pressure in the suction means is measured when the suction means attracts the film under a suction force, judging the attracting state of the suction means on the basis of the result of the measurement and controlling the part of the steps which is effected with the film held by the suction means on the basis of the judgment.

In one embodiment of the present invention, the attracting state of the suction means is indicated by a visual and/or acoustic means such as a monitor, a LED or a buzzer.

In another embodiment of the present invention, air is blown outside the suction means through the portion on which the suction means attracts the film.

In this embodiment, air may be blown at any timing. For example, air may be blown when an abnormality occurs or may be blown at regular intervals.

The term "attracting state of the suction means" means the state of maintenance of the suction means itself and the state of attraction of the suction means for the film.

In the method of the present invention, the change of pressure in the suction means (e.g., the suction pads and the horseshoe-like suction means used in the biochemical analysis apparatus) when the suction means attracts the frameless chemical analysis film under suction force.

The change of the pressure shows a peculiar pattern according to the attracting state of the suction means. For example, when the attracting force of the suction means is normal and the state of attraction of the suction means for the film is normal, the pressure in the suction means is lowered to a predetermined value within a predetermined time after initiation of attraction of the suction means for the film, and then kept at the predetermined pressure.

When a leak occurs in the vacuum pump or the vacuum line for the suction means, or the vacuum line clogs, the pressure in the suction means cannot be lowered to the predetermined value within the predetermined time after initiation of attraction of the suction means for the film. Further when the film is attracted to the suction means in a wrong position, the pressure in the suction means fluctuates after it is lowered to the predetermined pressure within the predetermined time.

Thus, the attracting state of the suction means can be known by monitoring the change of the pressure in the suction means, and the biochemical analysis apparatus can be properly controlled according to the attracting state of the suction means. For example, the succeeding steps of the biochemical analysis apparatus may be interrupted or the suction means may be cleaned before the succeeding step when the attracting state of the suction means is abnormal.

Further when the attracting state is indicated by a visual and/or acoustic means such as a monitor, a LED or a buzzer, the operator can instantly know that the attracting state of the suction means is abnormal and can quickly deal with the trouble.

Further, when air is blown outside the suction means through the portion on which the suction means attracts the film, dust or the like in the suction means can be blown out, whereby maintenance of the suction means is facilitated.

It is preferred that air be blown not only when an abnormality occurs but also at regular intervals.

BRIEF DESCRIPTION OF THE DRAWINGS

FIG. 7 is a block diagram for illustrating the pressure detecting system connected to the suction pad, and FIGS. 8A to 8D are graphs of various patterns of the pressure change in the suction pad.

DESCRIPTION OF THE PREFERRED EMBODIMENT

Figure 2:
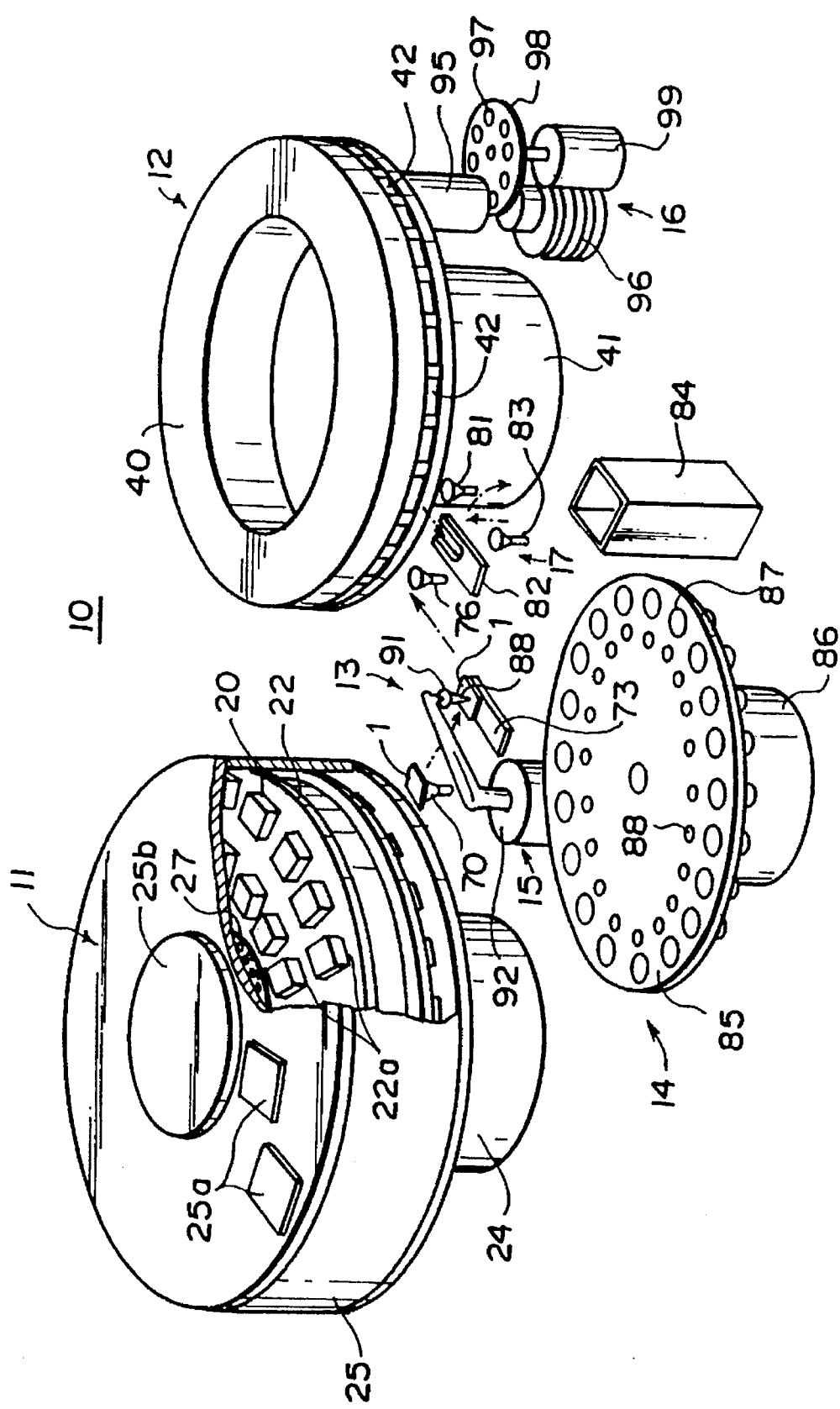
FIG. 2 is a schematic perspective view showing an example of a biochemical analysis apparatus for carrying out the method.

In FIG. 2, a biochemical analysis apparatus 10 for carrying out the method in accordance with an embodiment of the present invention comprises a film supplier 11 in which a plurality of virgin rectangular frameless chemical analysis films 1 are stored, an incubator 12 which is disposed beside the film supplier 11 and incubates the frameless chemical analysis films 1 at a predetermined temperature for a predetermined time, a film transfer means 13 which transfers the frameless chemical analysis films 1 from the film supplier 11 to the incubator 12, a sample liquid supplier 14 in which a plurality of sample liquids such as serum, urine or the like are stored, a spotting mechanism 15 which spots one of the sample liquids in the sample liquid supplier 14 on the frameless chemical analysis film 1 on the way to the incubator 12, and a light measuring system 16 disposed below the incubator 12.

Figure 3:
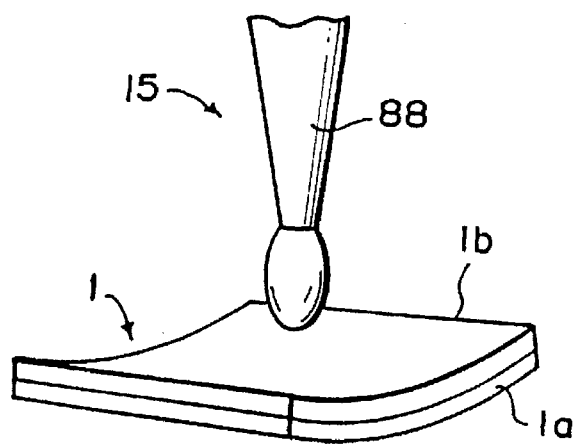
FIG. 3 is a perspective view showing spotting of the sample liquid on the frameless chemical analysis film.

As shown in FIG. 3, the frameless chemical analysis film 1 comprises a light-transmissive support sheet 1a formed of plastic film such as polyethylene terephthalate and a reagent layer 1b (including a spreading layer) formed on the support sheet 1a. If necessary, a wear-resistant protective layer of fibrous material such as fabric may be formed on the reagent layer 1b. Such a protective layer may double as the spreading layer.

The dry frameless chemical analysis film 1 is apt to curl toward the reagent layer 1b in the dry state before spotting of the sample liquid, and the curvature varies depending on the dryness and the kind of the reagent layer 1b. The reagent layer 1b contains reagent (chemical analysis reagent or immunoassay reagent) which makes coloring reaction when it is mixed with a particular component in the sample liquid spotted by a nozzle tip 88 of the spotting mechanism 15 and is incubated at a constant temperature for a predetermined time. A plurality of kinds of frameless chemical analysis films 1 having different reagent layers 1b are prepared according to the items of analysis, e.g., the chemical components or solid components to be analyzed in the sample liquids.

Figure 1:
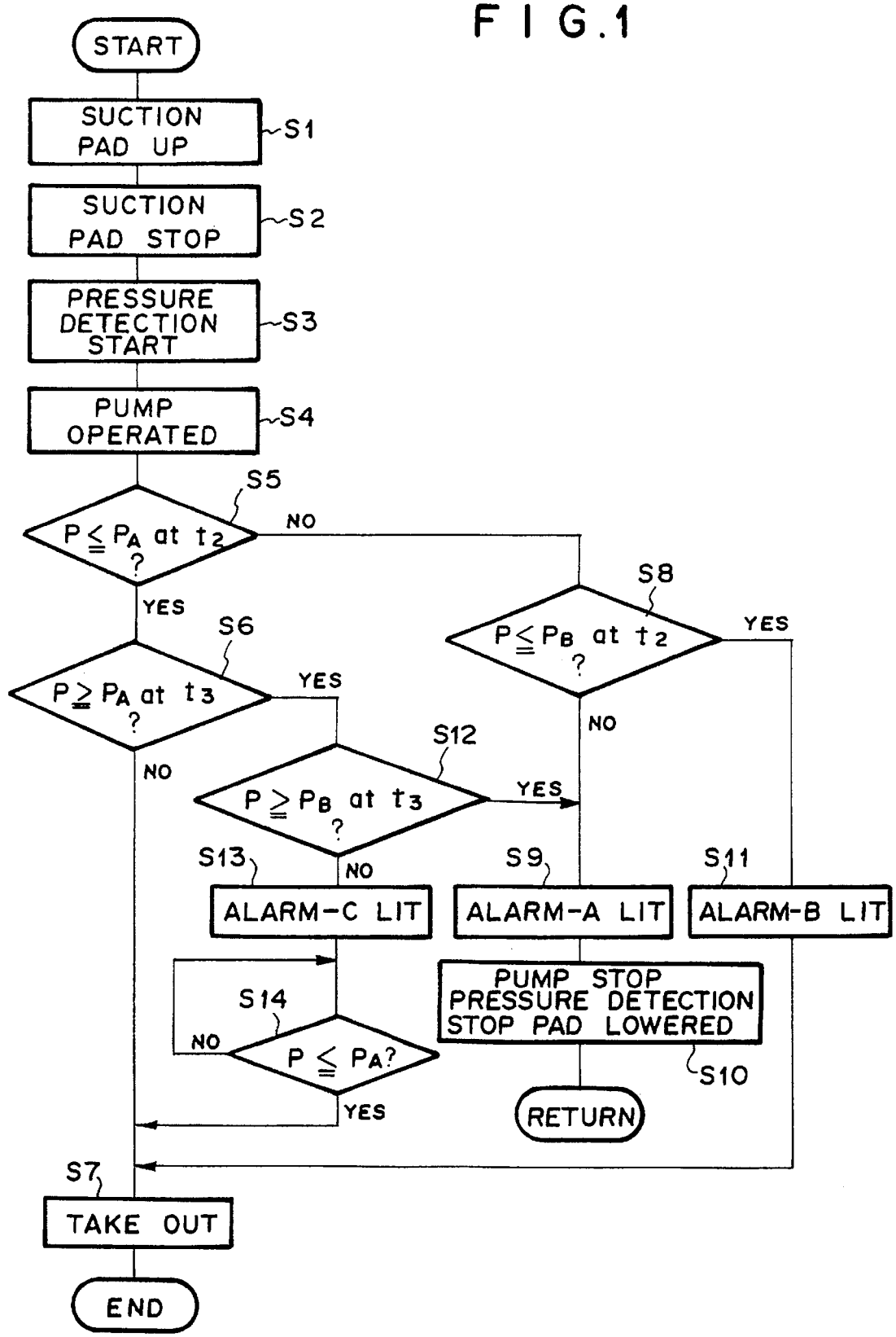
FIG. 1 is a flow chart for illustrating the method of controlling a biochemical analysis apparatus in accordance with an embodiment of the present invention.

The frameless chemical analysis films 1 are stored in cartridges 20 (FIG. 4) for the respective items of analysis. In the cartridge 20, a plurality of the frameless chemical analysis films 1 are stacked with the support sheets 1a facing downward. As shown in FIG. 1, the film supplier 11 is provided with a plurality of cartridge holding portions 22a which are arranged in inner and outer circles on a disk-like support 22 and a plurality of cartridges 20 loaded with the frameless chemical analysis films 1 are held in the respective cartridge holding portions 22a. The support 22 is supported for rotation on a base portion 24 and is rotated by a motor not shown so that a predetermined cartridge holding portion 22a is brought to a film takeout position where the film transfer means 13 takes out a frameless chemical analysis film 1 from the cartridge 20.

The support 22 is provided with a cover 25 which encloses inner space of the film supplier 11. The cover 25 is provided with a pair of openings 25a provided with lids and the cartridges 20 can be taken out and inserted into the cartridge holding portion 22a through the openings 25a. A dehumidifying agent holding portion 27 is formed in the support 22 at the center thereof and a dehumidifying agent is loaded in the dehumidifying agent holding portion 27 through an opening 25b formed in the cover 25. The opening 25b is provided with a lid. Thus the inner space of the film supplier 11 is kept dry. A film takeout port (not shown) is provided in the lower surface of the cover 25 in the film takeout position and a shutter is provided to open and close the film takeout port. The shutter is opened when the frameless chemical analysis film 1 is taken out from the cartridge 20 and a suction pad 70 of the film transfer means 13 is inserted into the film supplier 11 through the shutter and takes out the lowermost film 1 in the cartridge 20.

The incubator 12 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The frameless chemical analysis films 1 are incubated in the cells 42.

The film transfer means 13 for transferring the frameless chemical analysis film 1 from the film supplier 11 to the incubator 12 comprises suction pad 70 which takes out the film 1 from the cartridge 20, a horseshoe-like film transfer member 73 which receives the film 1 held on the suction pad 70 from below the film 1 with the reagent layer 1b facing upward and inserts the film 1 into the cell 42 in the incubator 12 through an opening which opens sideways, and a suction member 76 which moves in and out the cell 42 from below the cell and receives the film 1 held by the film transfer member 73 inside the cell 42.

Figure 4:
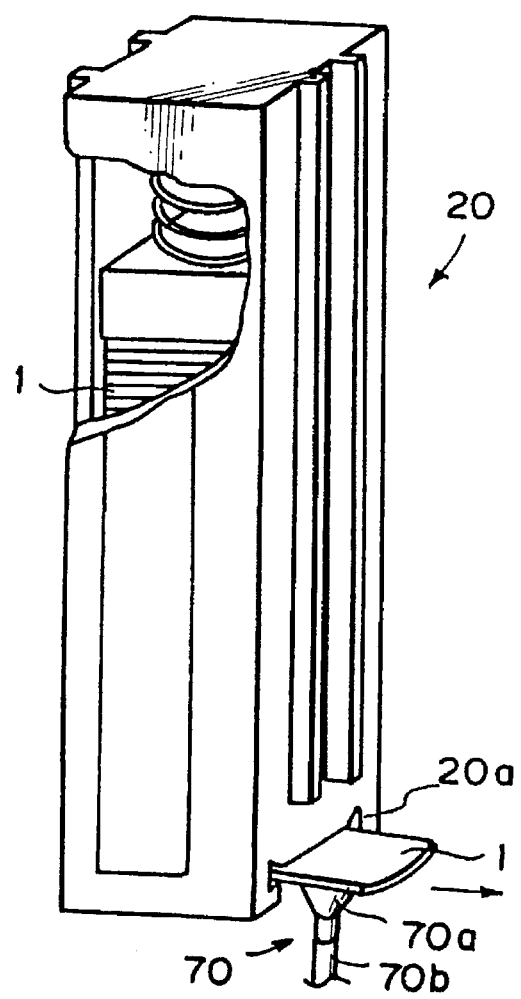
FIG. 4 is a perspective view showing the operation of taking out the frameless chemical analysis film from the cartridge.

As shown in FIG. 4, the suction pad 70 comprises a suction cup 70a which is directed upward and attracts the lower side of the support sheet 1a of the frameless chemical analysis film 1. The suction cup 70a is supported on a base portion 70b which is moved back and forth and up and down by a drive mechanism (not shown) and is connected to a suction pump (not shown) through a vacuum tube.

The suction pad 70 is moved upward into the cartridge 20 through an opening in the bottom of the cartridge 20 and attracts the lowermost frameless chemical analysis film 1 on the support sheet side thereof. Then the suction pad 70 is slightly moved downward to curl the lowermost film 1 and then horizontally moved to take out the film 1 from the cartridge through an opening 20a in the side wall of the cartridge with the film 1 held in the curled state. Thereafter the suction pad 70 is moved downward outside the film supplier 11 through the film takeout port in the film supplier 11 and is moved toward the spotting position where the sample liquid is spotted on the film 1.

Figure 5:
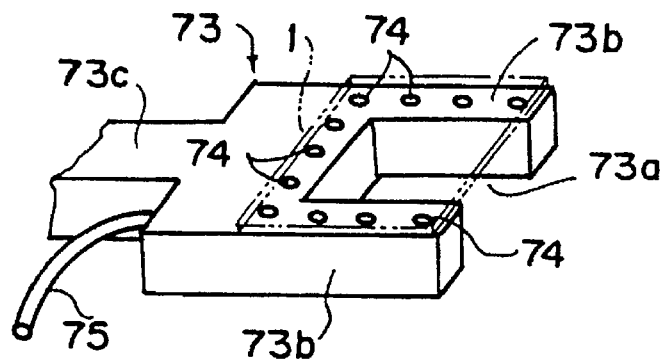
FIG. 5 is a fragmentary perspective view of the film transfer member.

As shown in FIG. 5, the film transfer member 73 is like a horseshoe in shape and has a flat upper surface. That is, the film transfer member 73 is bifurcated in the front end portion to form a pair of arm portions 73b extending on opposite sides of a cutaway portion 73a, and a plurality of suction holes 74 are formed to surround the cutaway portion 73a and to open in the upper surface of the film transfer member 73. The suction holes 74 are connected to a suction pump (to be described later) through a vacuum tube 75. The base portion of the film transfer member 73 is connected to a drive mechanism (not shown) to be inserted into the cell 42 in the incubator 12 through the opening thereof.

Figure 6A:
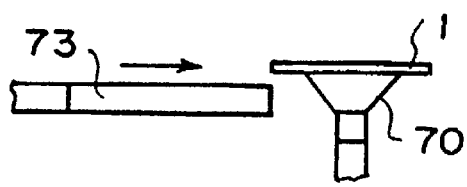
FIGS. 6A to 6C are schematic views for illustrating procedure for transferring the film from the suction pad to the film transfer member.
Figure 6B:
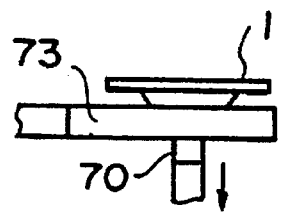
Figure 6C:
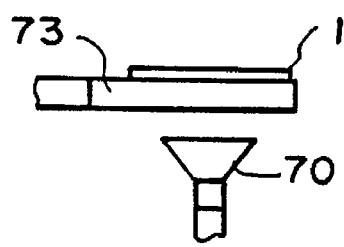

When the film transfer member 73 receives the film 1 from the suction pad 70, the film transfer member 73 is moved toward the suction pad 70 holding the film 1 as shown in FIG. 6A and is stopped in a position where the suction pad 70 is in the cutaway portion 73a of the film transfer member 73 with the film 1 positioned above the cutaway portion 73a as shown in FIG. 6B. Then the suction pad 70 is moved downward below the film transfer member 73 leaving the film 1 on the film transfer member 73 as shown in FIG. 6C. The film 1 left on the film transfer member 73 is held thereon under the suction force provided through the suction holes 74 in the arm portions 73b and the base portion of the transfer member 73. When the position of the suction pad 70 relative to the film 1 held thereby is accurately controlled, the position of the film transfer member 73 relative to the film 1 can be accurately controlled and a predetermined amount of the sample liquid can be accurately spotted on the center of the reagent layer 1b of the frameless chemical analysis film 1 held by the film transfer member 73.

A film removing means 17 (FIG. 1) is disposed in the film removing position of the incubator 12. The film removing means 17 comprises a removing suction pad 81 which attracts the film 1 in the cell 42 which has finished with measurement and lifts it, a horseshoe-like film removing member 82 which receives the film 1 from the removing suction pad 81 and transfers it outside the incubator 12 and a discarding suction pad 83 which receives the film 1 from the film removing member 82 and discards it into a discarding box 84.

The sample liquid supplier 14 comprises a turn table 85 which is rotated by a drive mechanism 86. The turn table 85 holds a plurality of sample tubes 87 filled with sample liquids which are arranged along the circumferential edge of the turn table 85 and is rotated to bring the sample tubes 87 to a sample liquid supplying position one by one. A plurality of nozzle tips 88 which are mounted on a spotting nozzle 91 to be described later are held on the turn table 85 inside the sample tubes 87.

The spotting means 15 for spotting the sample liquid on the frameless chemical analysis film 1 to be transferred to the incubator 12 comprises a spotting nozzle 91 which sucks and discharges the sample liquid, and a nozzle tip 88 is demountably mounted on the nozzle 91. The nozzle 91 is moved up and down and rotated by a drive mechanism 92. That is, the nozzle 91 sucks the sample liquid from the sample liquid supplier 14, is moved to the film 1 held by the film transfer member 73, and then spots the sample liquid on the film 1. The nozzle tip 88 is changed every time the sample liquid is changed.

The film 1 spotted with the sample liquid is transferred to the incubator 12 and incubated there.

After incubation for a predetermined time, the optical density of the reagent layer 1b is measured by the light measuring system 16 (FIG. 1) disposed below the incubator 12. The light measuring system 16 comprises said light measuring head 95 for measuring the optical density of the color formed by the coloring reaction between the reagent layer 1b and the sample liquid. The light measuring head 95 projects measuring light containing light of a predetermined wavelength onto the reagent layer 1b through the support sheet 1a and detects reflected light with a photodetector. Light from a light source (lamp) 96 enters the light measuring head 95 through a filter 97 and is caused to impinge upon the reagent layer 1b by the head 95. A plurality of kinds of the filters 97 are mounted on a rotary disk 98 which is driven by an electric motor 99 and one of the filters 97 is selected according to the item of measurement.

The reflected light from the reagent layer 1b carries thereon optical information (more particularly the amount of light) on the amount of coloring matter formed by the coloring reaction between the reagent layer 1b and the sample liquid. The reflected light is received by the photodetector and the optical information carried by the reflected light is converted to an electric signal by the photodetector. The electric signal is input into a determination section through an amplifier. The determination section determines the optical density of the coloring matter formed by the coloring reaction between the reagent layer 1b and the sample liquid on the basis of the level of the electric signal and determines the concentration of a predetermined chemical component in the sample liquid.

As can be understood from the description above, in the biochemical analysis apparatus 10, there are used many suction means, e.g., the suction pads 70, 76, 81 and 83 and the horseshoe-like transfer members 73 and 82.

This is because it is difficult to use the film holding means for the conventional chemical analysis system as it is to handle the curled frameless chemical analysis film 1 in an automated system. That is, the step of taking out the films 1 one by one from the cartridge in the film supplier 11, the step of spotting the sample liquid on the film 1 and transferring it to the incubator 12, the step of inserting the film 1 into the cell 42, the step of taking out the film 1 from the cell 42 after a predetermined time and discarding it and the like should be effected taking into account the curled shape of the film 1. Further use of such suction means is effective to handle the frameless chemical analysis film 1 without damaging the surface of the film 1.

However the suction means are connected to a vacuum pump through a vacuum line and when the vacuum line clogs with dust or the like or a leak occurs in the vacuum line or the vacuum pump, the attracting force of the suction means can be reduced, which makes it difficult to effect the steps described above in an optimal manner. Further, shift of the film 1 attracted by the suction means from the predetermined position gives rise to problems in the succeeding steps. Since many suction means are employed in the biochemical analysis apparatus 10, it is difficult for the operator to constantly check the states of the suction means and the position of the film 1 one by one.

In order to overcome these problems, a pressure detecting circuit and a pressure judging means are connected to the vacuum line for each suction means as shown in FIG. 7 and the attracting state of each suction means is watched.

FIG. 7 shows an attracting state judging system connected to the vacuum line for the suction pad 70 for taking out the film 1 from the cartridge 20. Similar attracting stake judging systems are connected to the other suction means, the suction pads 76, 81 and 83 and the horseshoe-like transfer members 73 and 82.

As described above, the suction pad 70 attracts the lowermost film 1 in the cartridge 20 by the suction cup 70a and moves in the transverse direction of the cartridge to take out the film 1 from the cartridge 20. The base portion 70b of the suction pad 70 is connected to a vacuum pump (P1) 101 and a pressure pump (P2) 110 by way of a pipe 100. A valve 102, a filter 103 and a pressure detecting portion 104 are provided between the vacuum pump 101 and the suction pad 70. A pressure sensor 105 is connected to the pressure detecting portion 104. The pressure detected by the pressure sensor 105 is read by a pressure detecting circuit 106 and the attracting state of the suction pad 70 is judged by an attracting state judging section 107 on the basis of the pattern of change of the pressure detected by the pressure sensor 105. When it is determined that the attracting state of the suction pad 70 is abnormal, one of LEDs 108A to 108C is lit and a predetermined sound is emitted from a buzzer 109 according to the degree of abnormality.

An air accumulating chamber 111 and a valve 112 are provided between the suction pad 70 and the pressure pump 110. The valve 112 is closed when the vacuum system is operated and is opened to blow off the dust or the like if any. When the valve 112 in the pressure system is opened the valve 102 in the vacuum system is closed.

The pressure system may be operated at any timing. For example, the pressure system may be operated when the attracting state judging section 107 judges that the attracting state of the suction pad 70 is abnormal or at regular intervals.

There is a predetermined correlation between the pattern of pressure change and the attracting state of the suction pad 70.

For example, when the suction pad 70 begins to attract the film 1 at time t1, and the pressure in the suction pad 70 is not higher than $P_A$ (a pressure at which the suction pad 70 can attract the film 1 under a sufficient force) at time t2 and is kept not higher than $P_A$ at time t3 as shown in FIG. 8A, the attracting state of the suction pad 70 is normal.

When the suction pad 70 begins to attract the film 1 at time t1, and the pressure in the suction pad 70 is still higher than a limit pressure $P_B$ (the critical pressure higher than which the suction pad 70 cannot attract the film 1) at time t2 as shown in FIG. 8B, the attracting state of the suction pad 70 is abnormal. That is, the vacuum system clogs with dust or the like or cracking is produced in the vacuum system.

When the suction pad 70 begins to attract the film 1 at time t1, and the pressure in the suction pad 70 is between $P_B$ and $P_A$ at time t2 and is kept at a pressure between $P_A$ and $P_B$ at time t3 as shown in FIG. 8C, it may be considered that the vacuum pump 101 has deteriorated, and prompt repair or replacement of parts of the vacuum pump 101 is necessary though the suction pad 70 can still attract the film 1.

Further, when the suction pad 70 begins to attract the film 1 at time t1, and the pressure in the suction pad 70 is not higher than $P_A$ at time t2 and subsequently increases to be higher than $P_A$ at time t3 as shown in FIG. 8D, it may be considered that though the vacuum system is operating normally, some abnormality, e.g., the film 1 is displaced from the predetermined position during the step of taking out the film 1 from the cartridge, occurs and the cause of the abnormality should be quickly removed.

The attracting state judging section 107 comprises a computer and various patterns of pressure change such as shown in FIGS. 8A to 8D are stored in a memory. The computer compares the pattern of pressure change input thereinto with the patterns of pressure change stored in the memory and selectively energizes the LEDs 8A to 8C and the buzzer 109 on the basis of the result of the comparison.

In this particular embodiment, the computer of the attracting state judging section 107 doubles as a controller for controlling the suction pad 70 and the like.

The operation of the computer will be described with reference to the flow chart shown in FIG. 1.

The computer first causes the suction pad 70 to move upward until the suction pad 70 abuts against the lowermost film 1 in the cartridge 20 through the opening in the bottom of the cartridge 20 and then stops the suction pad 70 there. (steps S1 and S2)

Then the computer causes the pressure detecting circuit 106 to initiate detecting the pressure P in the suction pad 70 (step S3) and causes the vacuum pump 101 to operate (step S4).

The computer watches the detected pressure P from the pressure detecting circuit 106 and judges whether the pressure P is not higher than $P_A$ at time t2. (step S5) It is assumed that the vacuum pump 101 is caused to operate at time t1.

When it is determined in step S5 that the pressure P is not higher than $P_A$ at time t2, the computer determines whether the pressure P is higher than $P_A$ at time t3. (step S6)

When it is determined in step S6 that the pressure P is higher than $P_A$ at time t3, the computer judges that the attracting state of the suction pad 70 is normal (corresponding to the pattern of pressure change shown in FIG. 8A), and causes the suction pad 70 to move in the transverse direction of the cartridge 20 to take out the film 1 through the film take-out port 20a of the cartridge 20. (step S7)

On the other hand, when it is determined in step S5 that the pressure P is higher than $P_A$ at time t2, the computer determines whether the pressure P is not higher than $P_B$ at time t2. (step S8) When it is determined in step S8 that the pressure P is higher than $P_B$ at time t2, the computer judges that the attracting state of the suction pad 70 is abnormal to such an extent that the step of taking out the film 1 cannot be successfully continued (corresponding to the pattern of pressure change shown in FIG. 8B), and causes the LED 108A to light up and the buzzer 109 to emit a predetermined sound (e.g., continuous sound). (step S9) Since the step of taking out the film 1 cannot be continued in this case, the computer stops the vacuum pump 101, causes the pressure detecting circuit 106 to interrupt detection of the pressure and lowers the suction pad 70 to the original position. (step S10)

The operator can know that the suction pad 70 is in a serious trouble from the LED 108A and the sound of the buzzer 109 and can properly and quickly deal with the trouble.

When it is determined in step S8 that the pressure P is not higher than $P_B$, the computer judges that the attracting force of the suction pad 70 is acceptable though not sufficient (corresponding to the pattern of pressure change shown in FIG. 8C), and causes the LED 108B to light up and the buzzer 109 to emit a predetermined sound (e.g., long on/off sound), thereby informing the operator of the need to promptly check the vacuum system. (step S11) Then the computer causes the suction pad 70 to move in the transverse direction of the cartridge 20 to take out the film 1 through the film take-out port 20a of the cartridge 20. (step S7)

When it is determined in step S6 that the pressure P is higher than $P_A$ at time t3, the computer determines whether the pressure P is higher than $P_B$ at time t3. (step S12) When it is determined in step S12 that the pressure P is not higher than $P_A$ at time t3, it may be considered that the film 1 is once properly attracted by the suction pad 70 in the predetermined position and the pressure P is lowered below $P_A$ and the film 1 is subsequently shifted from the predetermined position and the pressure P is increased to some extent (corresponding to the pattern of pressure change shown in FIG. 8D).

In this case, the computer causes the LED 108C to light up and the buzzer 109 to emit a predetermined sound (e.g., a short on/off sound) (step S13) and then idles until P lowers below the pressure $P_A$ (step S14). When the operator removes the cause of the abnormality and P lowers below the pressure $P_A$, the computer causes the suction pad 70 to move in the transverse direction of the cartridge 20 to take out the film 1 through the film take-out port 20a of the cartridge 20. (step S7)

When it is determined in step S12 that the pressure P is higher than $P_B$ at time t3, the computer judges that a serious abnormality, e.g., that the film 1 falls off the suction pad 70, occurs and causes the LED 108A to light up and the buzzer 109 to emit the predetermined sound in step S7 as in the case where the pressure P does not ever lower below the pressure $P_A$. (step S9)

Although, in the embodiment described above, the attracting state of the suction pad 70 is judged from the pattern of the pressure change in the vacuum system, other states may be judged from the pattern of the pressure change in the vacuum system.

For example, by watching the pressure changes in the vacuum systems for the suction pad 70 and the transfer member 73 when the film 1 is transferred from the former to the latter, it can be judged what timing the film 1 is transferred or whether the film 1 is surely transferred.

The method of the present invention may be variously modified without being limited to the embodiment described above. For example, the pressure system may be eliminated from the apparatus shown in FIG. 1 and the attracting state may be judged on the basis of patterns of pressure change other than those shown in FIGS. 8A to 8D.

Although, in the embodiment described above, the state of abnormality is indicated by use of LEDs, the state of abnormality may be indicated by use of a monitor.

As can be understood from the description above, in accordance with the present invention, the pressure change in the vacuum system for the suction means such as the suction pads or the horseshoe-like transfer members is monitored and the attracting state of the suction means is judged on the basis of the pattern of the pressure change, and the biochemical analysis apparatus is controlled according to the attracting state of the suction means thus judged. Accordingly, in the biochemical analysis apparatus in which a suction means is employed which is apt to fail due to the adhesion of dust, a crack in the line, etc., the failure can be detected soon and dealt with properly, whereby the biochemical analysis apparatus can be smoothly operated.

Further, when the attracting state is indicated by a visual and/or acoustic means such as a monitor, a LED or a buzzer, the operator can instantly know that the attracting state of the suction means is abnormal and can quickly deal with the trouble.

Further, when air is blown outside the suction means, dust or the like in the suction means can be blown out, whereby the biochemical analysis apparatus can be further smoothly operated.

What is claimed is:

1. A method of controlling a biochemical analysis apparatus comprising the steps of:

moving an analysis film between a plurality of processing stations, and temporarily holding said analysis film at said processing stations, wherein at least two of said moving and holding steps are performed using at least two of a plurality of independent suction means, measuring a pressure in said independent suction means at least two predetermined times after said independent suction means begins attracting said film under a suction force, judging an attracting state of said independent suction means on the basis of the result of the measurements and a predetermined set of attracting state parameters wherein said attracting state parameters are used to indicate at least two different abnormal states, and controlling said moving and holding steps on the basis of the judgment.

2. A method of controlling a biochemical analysis apparatus as defined in claim 1 in which the steps of judging the attracting state of the suction means is performed on the basis of a change of pressure with time.

3. A method of controlling a biochemical analysis apparatus as defined in claim 2 in which the attracting state of the suction means is indicated by a visual and/or acoustic means.

4. A method of controlling a biochemical analysis apparatus as defined in claim 1 in which the attracting state of the suction means is indicated by a visual and/or acoustic means.

5. A method of controlling a biochemical analysis apparatus as defined in any one of claims 1 to 4 in which air is blown outside the suction means through a portion of said suction means on which the suction means attracts the film when judgment that the attracting state is abnormal is made according to said predetermined attracting state parameters.

6. A method in accordance with claim 1, wherein said judging step further comprises the step of determining whether said independent suction means is at least partially obstructed.

7. A method in accordance with claim 1, wherein said judging step further comprises the step of comparing a pattern of pressure measurements at said predetermined times with a predetermined pattern of pressure values for said predetermined times, said predetermined pattern defined by said predetermined set of attracting state parameters.

8. A method of controlling a biochemical analysis apparatus comprising the steps of:

moving an analysis film to and from at least one processing station, and temporarily holding said analysis film at said processing station, wherein at least one of said moving and holding steps is performed using at least one suction means, measuring a pressure in said suction means at least two predetermined times after said suction means begins attracting said film under a suction force, judging an attracting state of said suction means on the basis of the result of the measurements and a predetermined set of attracting state parameters wherein said attracting state parameters are used to indicate at least two different abnormal states, and controlling said apparatus on the basis of the judgment.

* * * * *